US010420565B2

(12) United States Patent
Garcia et al.

(10) Patent No.: US 10,420,565 B2
(45) Date of Patent: Sep. 24, 2019

(54) CINCH AND POST FOR TRICUSPID VALVE REPAIR

(71) Applicant: Abbott Cardiovascular Systems Inc., Santa Clara, CA (US)

(72) Inventors: Antonio N. Garcia, San Jose, CA (US); Laura M. Kalvass, Mountain View, CA (US); Sean A. McNiven, Menlo Park, CA (US); Benjamin L. Lee, Santa Clara, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 297 days.

(21) Appl. No.: 15/364,169

(22) Filed: Nov. 29, 2016

(65) Prior Publication Data

US 2018/0146964 A1    May 31, 2018

(51) Int. Cl.
*A61B 17/122*    (2006.01)
*A61B 17/00*    (2006.01)
(Continued)

(52) U.S. Cl.
CPC ...... *A61B 17/122* (2013.01); *A61B 17/00234* (2013.01); *A61B 17/083* (2013.01); *A61B 17/10* (2013.01); *A61B 17/1285* (2013.01); *A61F 2/2454* (2013.01); *A61F 2/2466* (2013.01); *A61B 17/0682* (2013.01); *A61B 17/08* (2013.01); *A61B 17/1227* (2013.01); *A61B 2017/00243* (2013.01); *A61B 2017/00292* (2013.01); *A61B 2017/0417* (2013.01);
(Continued)

(58) Field of Classification Search
CPC ............ A61B 17/122; A61B 17/00234; A61B 17/1285; A61B 17/10; A61B 17/083; A61F 2/2466
See application file for complete search history.

(56) References Cited

U.S. PATENT DOCUMENTS 5,171,259 A    12/1992    Inoue
5,607,445 A     3/1997    Summers
(Continued)

FOREIGN PATENT DOCUMENTS

WO    WO 91/15155 A1     10/1991
WO    WO 2004/069055 A2    8/2004
(Continued)

OTHER PUBLICATIONS

European Patent Office, International Search Report, dated Jan. 29, 2018, pp. 1-4.
(Continued)

*Primary Examiner* — Richard G Louis
(74) *Attorney, Agent, or Firm* — Baker Botts L.L.P.

(57) ABSTRACT

A system for repairing a tricuspid valve in a patient's heart comprising a post having a distal end and a proximal end, a capture element attached to the distal end of the post, the capture element including: a plurality of arms each having a first end and a second end, each arm attached at the first end to the post and extending both radially outwardly from the post and proximally, each arm defining an opening at the second end; a wire passing sequentially through the opening on each arm, whereby tensioning the wire draws the second end of each arm towards the post.

16 Claims, 6 Drawing Sheets

(51) Int. Cl.
- *A61B 17/128* (2006.01)
- *A61B 17/08* (2006.01)
- *A61B 17/10* (2006.01)
- *A61F 2/24* (2006.01)
- *A61B 17/068* (2006.01)
- *A61B 17/04* (2006.01)

(52) U.S. Cl.
CPC ............ *A61F 2/246* (2013.01); *A61F 2/2439* (2013.01); *A61F 2230/005* (2013.01); *A61F 2230/0052* (2013.01); *A61F 2230/0093* (2013.01); *A61F 2250/001* (2013.01)

(56) References Cited

U.S. PATENT DOCUMENTS

| | | | |
|---|---|---|---|
| 5,924,424 | A | 7/1999 | Stevens et al. |
| 6,129,758 | A | 10/2000 | Love |
| 7,112,207 | B2 | 9/2006 | Allen et al. |
| 7,563,267 | B2 | 7/2009 | Goldfarb et al. |
| 7,563,273 | B2 | 7/2009 | Goldfarb et al. |
| 7,569,062 | B1 | 8/2009 | Kuehn et al. |
| 7,666,204 | B2 | 2/2010 | Thornton et al. |
| 8,470,028 | B2 | 6/2013 | Thornton et al. |
| 8,753,362 | B2 | 6/2014 | Widomski et al. |
| 9,180,005 | B1 | 11/2015 | Lashinski et al. |
| 9,750,505 | B2 | 9/2017 | Miles et al. |
| 9,770,232 | B2 | 9/2017 | Amin et al. |
| 2002/0013571 | A1* | 1/2002 | Goldfarb ........ A61B 17/00234 606/1 |
| 2003/0018358 | A1* | 1/2003 | Saadat ............... A61B 17/0401 606/232 |
| 2003/0139819 | A1 | 7/2003 | Beer et al. |
| 2004/0073242 | A1 | 4/2004 | Chanduszko |
| 2004/0176799 | A1 | 9/2004 | Chanduszko et al. |
| 2004/0220610 | A1 | 11/2004 | Kreidler et al. |
| 2005/0043759 | A1 | 2/2005 | Chanduszko |
| 2005/0065548 | A1 | 3/2005 | Marino et al. |
| 2005/0273135 | A1 | 12/2005 | Chanduszko et al. |
| 2005/0288786 | A1 | 12/2005 | Chanduszko |
| 2006/0122646 | A1 | 6/2006 | Corcoran et al. |
| 2006/0265004 | A1 | 11/2006 | Callaghan et al. |
| 2006/0271089 | A1 | 11/2006 | Alejandro et al. |
| 2007/0010851 | A1 | 1/2007 | Chanduszko |
| 2007/0027533 | A1 | 2/2007 | Douk |
| 2007/0073337 | A1 | 3/2007 | Abbott et al. |
| 2007/0112380 | A1 | 5/2007 | Figulla et al. |
| 2007/0167981 | A1 | 7/2007 | Opolski et al. |
| 2007/0179527 | A1 | 8/2007 | Eskuri et al. |
| 2007/0250081 | A1 | 10/2007 | Cahill et al. |
| 2007/0260305 | A1 | 11/2007 | Drews et al. |
| 2009/0188964 | A1 | 7/2009 | Orlov |
| 2010/0004740 | A1 | 1/2010 | Seguin et al. |
| 2010/0234878 | A1 | 9/2010 | Hruska et al. |
| 2010/0234885 | A1 | 9/2010 | Frazier et al. |
| 2011/0060407 | A1 | 3/2011 | Ketai et al. |
| 2011/0276086 | A1 | 11/2011 | Al-Qbandi et al. |
| 2013/0066341 | A1* | 3/2013 | Ketai ................... A61B 17/08 606/151 |
| 2013/0282110 | A1 | 10/2013 | Schweich, Jr. et al. |
| 2013/0289718 | A1 | 10/2013 | Tsukashima et al. |
| 2014/0005778 | A1 | 1/2014 | Buchbinder et al. |
| 2014/0163669 | A1 | 6/2014 | Ben-zvi et al. |
| 2014/0200662 | A1 | 7/2014 | Eftel et al. |
| 2015/0066077 | A1 | 3/2015 | Akpinar |
| 2015/0173765 | A1 | 6/2015 | Miller et al. |
| 2016/0022417 | A1 | 1/2016 | Karapetian et al. |
| 2016/0030169 | A1 | 2/2016 | Shahriari |
| 2018/0055633 | A1 | 3/2018 | Costello et al. |

FOREIGN PATENT DOCUMENTS

| | | |
|---|---|---|
| WO | WO 2004/069055 A3 | 8/2004 |
| WO | WO 2014/018907 A1 | 1/2014 |
| WO | WO 2014/182849 A1 | 11/2014 |

OTHER PUBLICATIONS

International Search Report dated Jun. 12, 2018 in International Application No. PCT/US2018/019033.

International Search Report dated Oct. 13, 2017 from International Application No. PCT/US2017/039811, European Patent Office ISA/EP.

Vismara et al., "Transcatheter Edge-to-Edge Treatment of Functional Tricuspid Regurgitation in an Ex Vivo Pulsatile Heart Model," JACC 68(10):1024-1033 (2016).

* cited by examiner

CINCH AND POST FOR TRICUSPID VALVE REPAIR

BACKGROUND

This invention relates to the repair of a tricuspid valve exhibiting valve regurgitation. More particularly, the invention relates to apparatus and methods suitable for a less invasive repair of a tricuspid heart valve.

Figure 1:
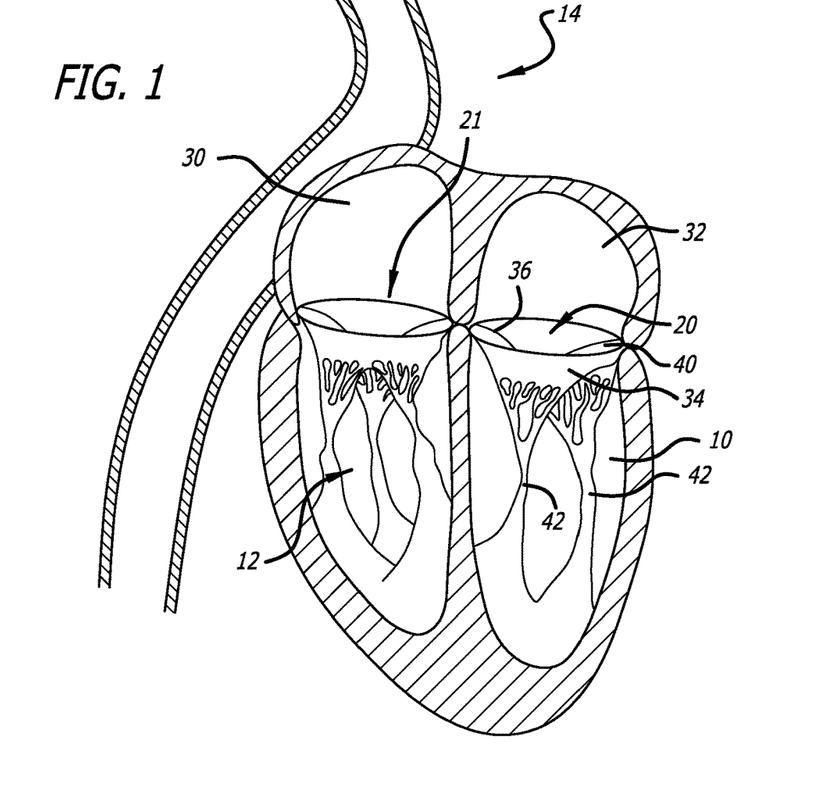
FIG. 1 is a cross-sectional view of the left and right ventricles of a human heart in diastole.

FIG. 1 is a cross-sectional view of the left and right ventricles of a human heart 14 in diastole. The figure shows how the tricuspid valve 21 connects together the chambers of the right atrium and the right ventricle, and controls the flow of blood between these two chambers.

Figure 2:
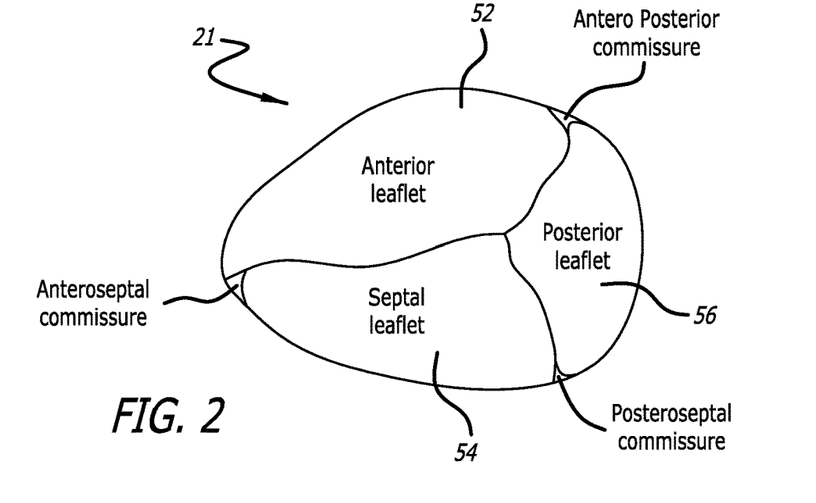
FIG. 2 is a schematic plan view of a tricuspid valve of a human heart, showing the three leaflets of the valve namely the anterior leaflet, posterior leaflet, and the septal leaflet, which all converge on a common point of meeting at the center of the valve.

FIG. 2 is a schematic view from above of a tricuspid valve of a human heart, showing the three leaflets of the valve namely the anterior leaflet 52, posterior leaflet 56, and the septal leaflet 54, which all converge on a common point of meeting at the center of the valve.

As used herein, the term "endovascular," refers to procedure(s) of the present invention that are performed with interventional tools and supporting catheters and other equipment introduced to the heart chambers from the patient's arterial or venous vasculature remote from the heart. The interventional tools and other equipment may be introduced percutaneously, i.e., through an access sheath, or may be introduced via a surgical cut down, and then advanced from the remote access site through the vasculature until they reach heart 14. As such, the methods and apparatus described herein generally do not require penetrations made directly through an exterior heart muscle, i.e., myocardium, although there may be some instances where penetrations will be made interior to the heart, e.g., through the interatrial septum to provide for a desired access route.

The atrioventricular valves are each located at a junction of the atria and their respective ventricles. The atrioventricular valve extending between the right atrium 30 and the right ventricle 12 has three valve leaflets (cusps) and is referred to as the tricuspid or right atrioventricular valve 21. The atrioventricular valve between the left atrium 32 and the left ventricle 10 is a bicuspid valve having only two leaflets or cusps 34 and is generally referred to as the mitral valve 20.

During operation of the heart 14, the valve leaflets open during diastole when the heart atria fill with blood, allowing the blood to pass into the ventricle. During systole, however, the valve leaflets are pushed together such that the free edges of the leaflets are closed against each other along a line of coaptation to prevent the back-flow of blood into the atria. Back flow of blood or "regurgitation" through the mitral valve 20 is facilitated to be prevented when the leaflets 34 are closed, such that the mitral valve 20 functions as a "check valve" which prevents back-flow when pressure in the left ventricle 10 is higher than that in the left atrium 32.

The mitral valve leaflets 34 are attached to the surrounding heart structure along an annular region referred to as the valve annulus 40. The free edges 36 of the leaflets 34 are secured to the lower portions of the left ventricle 10 through tendon-like tissue structures, known as chordae tendineae or chordae 42. The chordae 42 are attached to the papillary muscles which extend upwardly from the lower portions of the left ventricle and interventricular septum 46.

The tricuspid valve is similar to the mitral valve, but it is more complex in that it has three leaflets, as described above.

Tricuspid regurgitation, i.e., backward leakage of blood at the tricuspid heart valve, is typically caused by defective coaptation of the three leaflets against each other, and results in reduced pumping efficiency. Diagnosis of tricuspid regurgitation can be performed using visualization with transesophageal echocardiography or by echocardiography. In particular, defective leaflet coaptation and the site and direction of the regurgitant flow can be examined to evaluate likely modes of failure.

Tricuspid valve prolapse, i.e. degeneration of tricuspid valve leaflets, is the most common cause of tricuspid regurgitation in North America. Many cases of regurgitation can be repaired by modifications of the original valve in a procedure generally referred to as valvuloplasty. Valves that are heavily calcified or significantly compromised by disease may need to be replaced.

Successful methods have been developed for performing less invasive repairs to the mitral valve. In particular, such repairs can be performed on a beating heart such that the patient does not have to be placed on cardiopulmonary bypass.

One approach suitable for mitral valve repair is to introduce instruments via a transcatheter procedure into the heart by direct introduction through a passageway through the wall of the heart. Suitable gripping and fastening instruments have appropriate dimensions to fit through the cardiac catheter into the heart. The methods typically include gripping the edges of the two leaflets of the mitral valve, and securing them together using clasping, stitching, or suturing techniques. By connecting the leaves of the mitral valve together over a short length, the loss of tension in the leaves is reduced, and the remaining portions of the leaves have better coaptation and better perform the function of a one way valve by not permitting blood to flow in the wrong direction by regurgitation. The same approach as taken in repairing the mitral valve has been tried for repairing the tricuspid valve using clasps such as the clasp of the MitraClip®.

However, methods for repairing the mitral valve do not apply conveniently to a method for repairing the tricuspid valve. One major difference is that while the mitral valve has only two leaflets extending parallel with each other and which are relatively easy to grasp simultaneously, the tricuspid valve has three leaflets 52, 54, 56 that come to a common point of meeting, as seen in FIG. 2. The mechanical problems involved in grasping all three leaflets simultaneously at a single point are far more complex than with the mitral valve, because the operator is not presented with two elongated edges to grasp, but with three triangulated points that must be grasped simultaneously. By successfully doing this, the tension in the leaflets is increased, and coaptation is improved.

Accordingly, there is a need in the art for a novel and advantageous method to grasp and connect the three leaves of the tricuspid valve at the common point of their meeting. The present invention addresses these, and other needs.

SUMMARY OF THE INVENTION

As may be understood with reference to the drawings and the detailed description of some embodiments, the invention comprises various embodiments, one of which is a system for repairing a tricuspid valve in a patient's heart. The system comprises: a post having a distal end and a proximal end wherein a capture element is attached to the distal end of the post. The capture element includes a plurality of arms each having a first end and a second end, each arm attached at the first end to the post and extending both radially outwardly from the post and proximally. Each arm defines an opening at the second end. A wire passes sequentially through the opening on each arm, so that tensioning the wire draws the second end of each arm towards the post. In some embodiments, the capture element includes a hoop having a continuous circumference sized to receive the distal end of the post. In other embodiments, the arms and the hoop of the capture element are formed from a single sheet of metal. Preferably, the single sheet of metal is a Nickel Titanium alloy. In some embodiments, an annular plug may be inserted between the post and the hoop. The plug between the post and the hoop may be formed by enlargement through applying a compression force across an axial dimension so as to expand a radial dimension of the plug. In further embodiments, the post defines a central bore having an orifice at the distal end of the post, and the wire passes into the bore through the orifice. In other embodiments, the post at the proximal end is removably attached to a delivery catheter by an attachment means. In further embodiments, the wire is attached to a zip tie by a frangible connection. In other embodiments, the capture element is foldable about the post and both the post and the capture element are inserted inside an inner bore of a delivery catheter.

The foregoing then describes a structure having features of the invention, which may be advantageously used for capturing three leaves of a tricuspid valve.

In other aspects, the invention comprises a method of repairing a tricuspid valve having a first leaflet, a second leaflet, and a third leaflet in a heart of a patient. The method comprises: passing an elongate post between the first leaflet, the second leaflet, and the third leaflet. This is followed by opening a wire into a circular shape that surrounds the post, thereby providing a space between the wire and the post. Then the post and the wire are manipulated until a tip of the first leaflet, a tip of the second leaflet, and a tip of the third leaflet are positioned within the space between the wire and the post. A tension force is applied to the wire, thereby reducing a circumference of the circular shape and thereby capturing simultaneously the tip of the first leaflet, the tip of the second leaflet, and the tip of the third leaflet between the post and the wire. In some embodiments, the wire is locked into a fixed final circumference. Locking the wire may include using a zip tie. Using a zip tie may, in some embodiments, include breaking a frangible connector that attaches the wire to the zip tie. In other embodiments, opening a wire into a circular shape may include releasing, from confinement, arms attached to the elongate post, wherein the arms carry the wire and are shaped to expand radially outwardly. In some embodiments, releasing from confinement includes withdrawing a sheath away from covering the arms. Preferably, embodiments may include removing a delivery catheter from the heart of the patient, while leaving the post and the wire in the heart. And, removing a delivery catheter from the heart of the patient may include disconnecting the post from the delivery catheter by withdrawing a sheath away from covering a portion of the post.

These and other advantages of the invention will be more clearly understood when read in conjunction with the drawings and the detailed description of some of the embodiments.

DETAILED DESCRIPTION OF THE PREFERRED EMBODIMENTS

In some embodiments, as more clearly understood with reference to the drawings, the invention is a system for repairing the tricuspid valve in the heart of a patient via a transcatheter procedure. An objective of the system is to provide a mechanism that securely grips all three of the leaflets of a tricuspid valve simultaneously, where all three leaflets meet at the center of the valve. As a consequence of this gripping connection, the tricuspid valve is converted into a valve having three separate orifices instead of only one orifice. However after being connected, the three orifices are formed by leaflets that close more completely during the systole and therefore more effectively fulfill a function of a one way fluid valve which is to prevent regurgitation.

Figure 3:
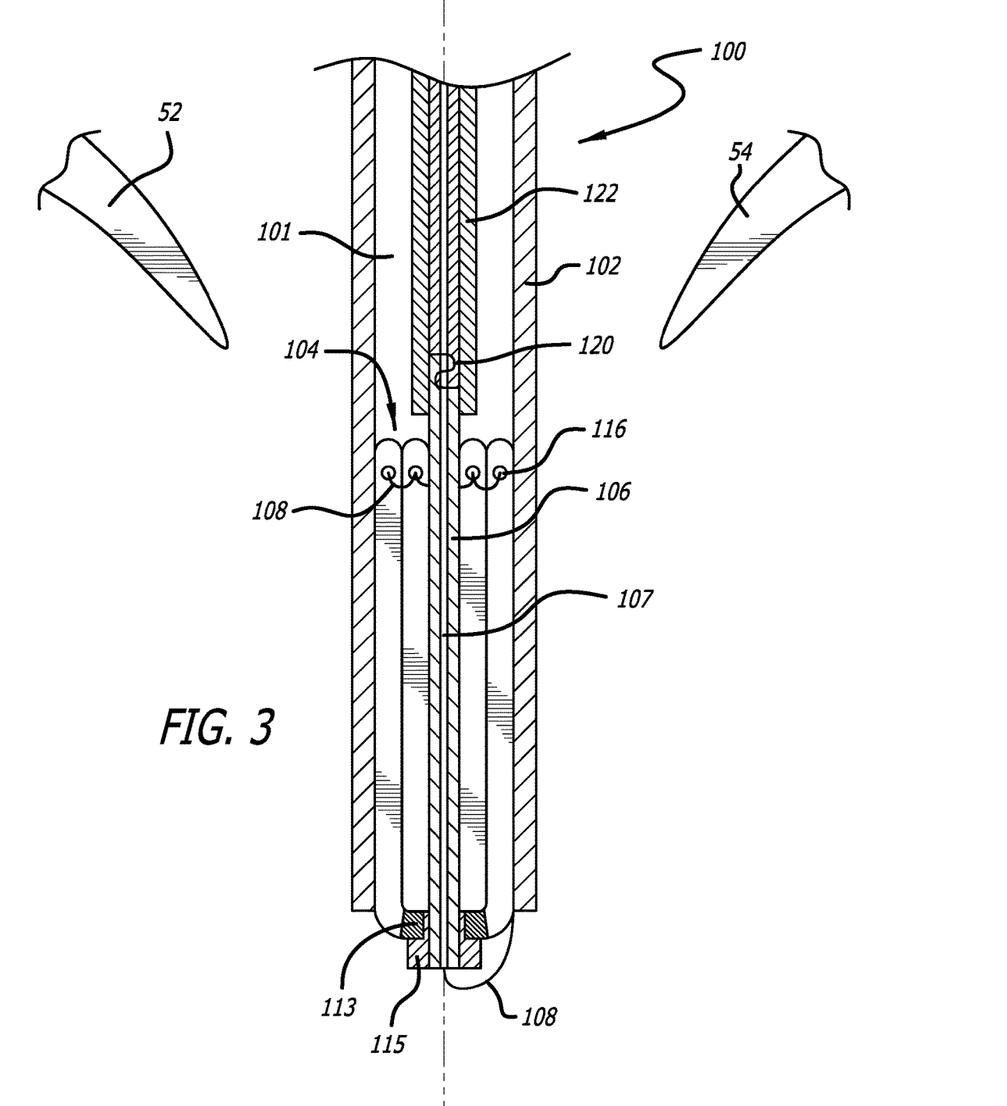
FIG. 3 is a sectional view of a system having features of the present invention, shown in a compressed condition for delivery.

FIG. 3 shows an exemplary system having features of the invention positioned at the distal end of a delivery catheter. The system is located at a distal end of a delivery catheter 100 which is configured, according to known means, to be deliverable to the right atrium of a patient's heart. The delivery catheter comprises an outer sheath 102, within which a device 104 is contained within a central bore of the sheath a device 104 configured to capture the three centrally located points of a tricuspid valve, and thereafter to be separated from the distal end of the catheter 100 and left behind in the patient's heart.

Centrally located in the device 104 is an elongate push element 106, which has the form of a rod extending from the distal end of the catheter all the way back to the proximal end (not shown in the figures) where it is controlled through known means by the user. The push element 106 defines a central bore 107 which is suitable for containing an activation wire 108 slideably extending from the distal tip of the push element to the proximal end of the push element under control of the user, and it has the function of activating the device 104 according to methodology set forth below.

Figure 4:
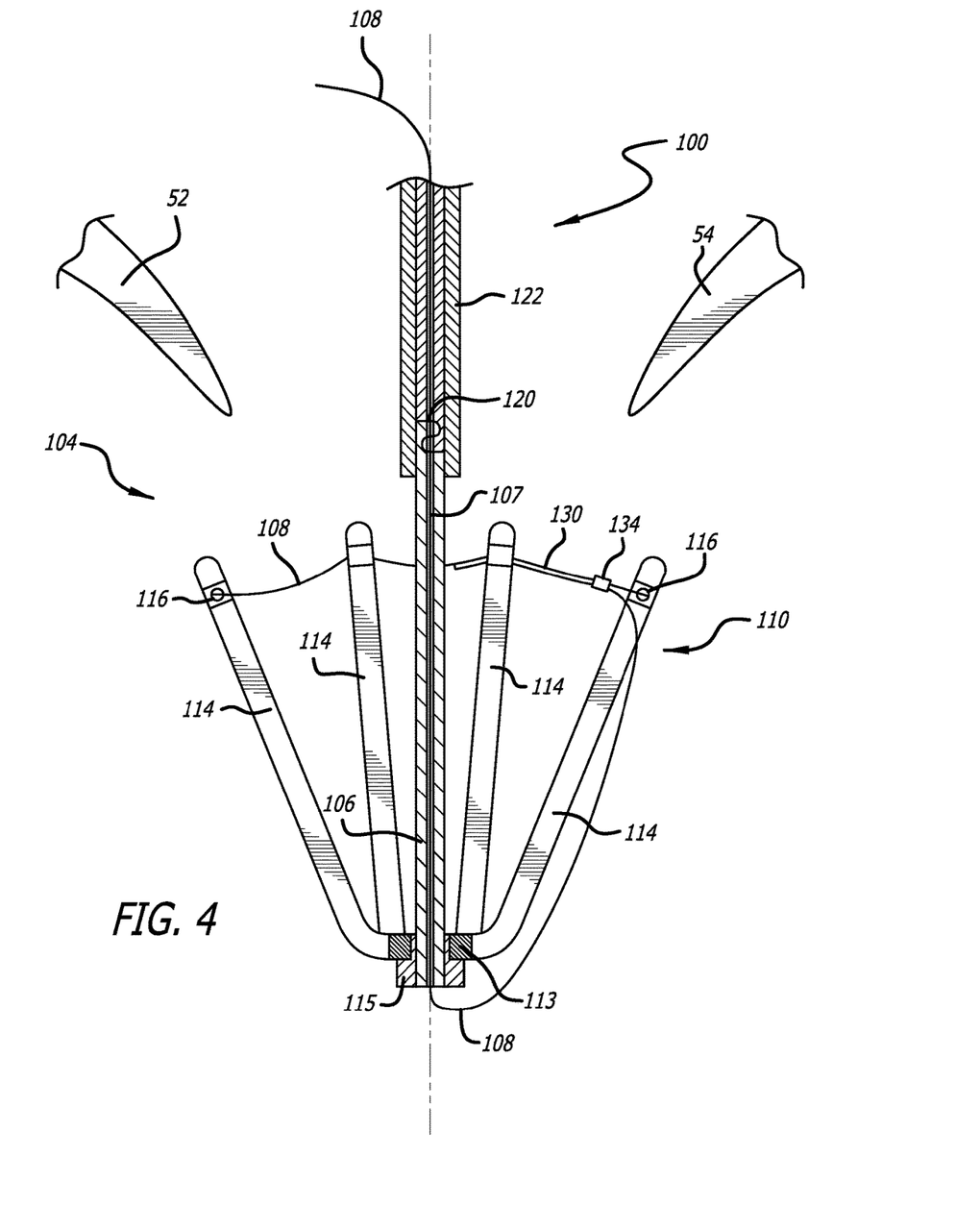
FIG. 4 is a sectional view of the system of FIG. 3, shown in an expanded condition.

As may be appreciated with reference to FIG. 3 and FIG. 4, the push element supports a capture element 110. The capture element is attached at its center to the distal tip of the push element 106. The capture element 110 may be formed by initially being cut from a planar sheet of metal, preferably shape memory Nitinol alloy, in a configuration exemplified in FIG. 5. At the center of the element is a continuously bounded circular opening 112, bound by a continuous hoop 113 of metal. From the opening 112, a plurality of arms 114 extend in a radially outward direction. The outer tip of each arm 114 defines a small hole 116 which is sized to receive, initially, the activation wire passing through each hole, and finally a zip tie that will be described below.

Figure 5:
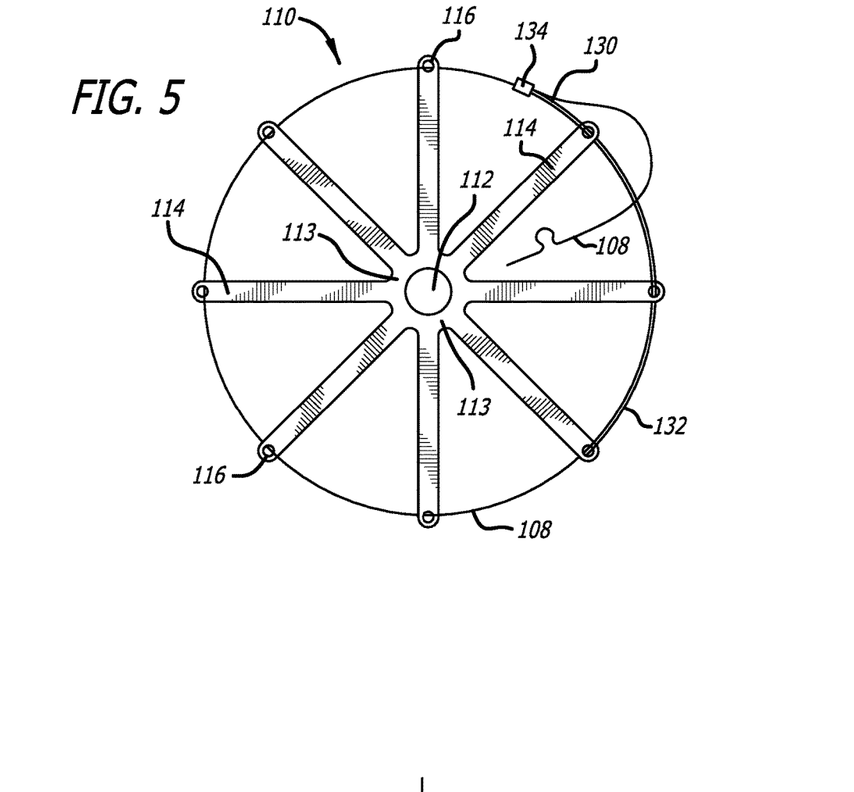
FIG. 5 is a plan view of a component of the invention, shown in a planar configuration during manufacture.

Once the capture element 110 has been cut from a planar sheet of metal, it is shaped by known means for heat treating shape memory alloys, into a shape that will provide a basket like receptacle for eventually receiving the three tips of three tricuspid leaflets 52, 54, 56 during a capture process. This basket like shape may be envisaged with reference to FIG. 4—which also shows leaflets 52, 54 prior to their being received into the basket like shape of the capture element 110.

Figure 6:
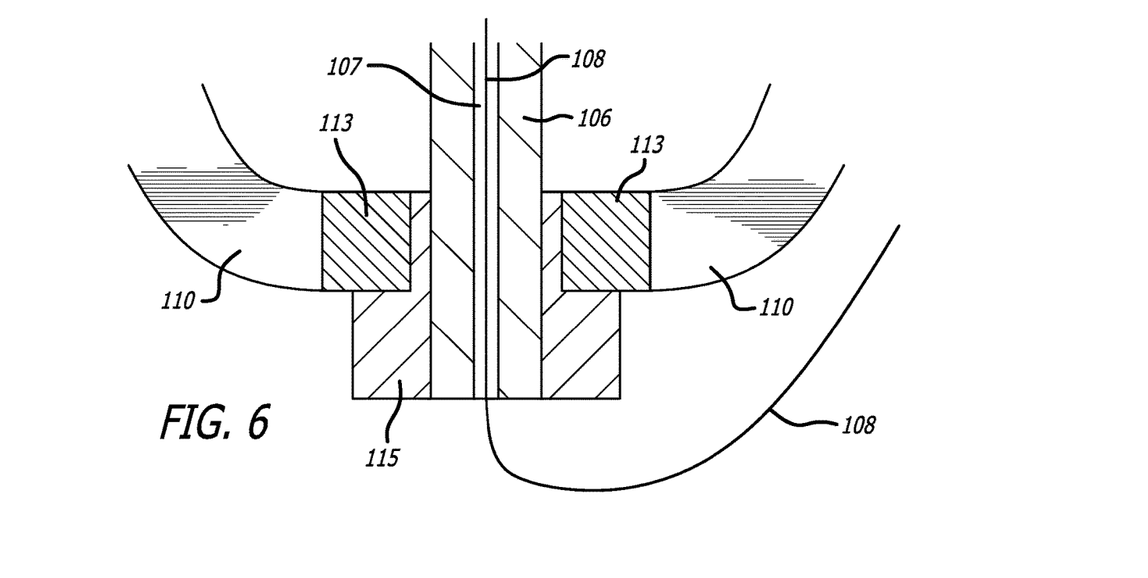
FIG. 6 is a detail view of a portion of the system seen circled in FIG. 4, marked with the numeral "6".

The capture element 110 may be attached to the push element 106 by means of an annular plug 115 which is sized to fit (at least partially) between the metal forming the hoop 113 of the circular opening 112 and the push element 106, as shown in detail in FIG. 6. Once the plug is inserted into the position seen in FIG. 6, it may be compressed in an axial direction to force both its internal radius and external radius to expand, and thus to become locked onto both the push element 104, and also onto the capture element 110. In this way, the capture element 110 may be securely attached to the push element 104.

During assembly of the device 104 and before it is inserted into the sheath 102 of the catheter, a cinching wire 108 is threaded through all the openings 116 at the ends of the radial arms 114 of the capture element 110, and a free end is threaded through the internal bore 107 of the push rod 106 all the way back to the proximal end of the catheter where it may be tensioned or relaxed by the operator. Thereafter, the capture element 110 is closed into a cylindrical shape, and is then pushed up inside the bore 101 of the catheter sheath 102. The system now has the general appearance of the system seen in FIG. 3. In this condition, it is ready for deployment.

A system for cinching and locking the capture element 110 in a closed condition after deployment is now described with reference to FIG. 4, FIG. 5 and FIG. 7. To this end, the cinching system for the capture element is fitted with a very thin zip tie 130 formed from an insoluble polymer, and this zip tie is threaded through the openings 116 in the arms 114 as seen in FIG. 4 and FIG. 5. As in the case of a typical zip tie that is known in the art, the tie 130 has a free end 132 at a first end, and a lock 134 at the opposite second end. Zip ties (also known as Cable Ties) are well known in the art, as exemplified by U.S. Pat. No. 5,956,813 and the art cited therein which are incorporated herein by reference. The free end 132 is eventually threaded through the lock 134 upon the activation wire 108 being tensioned, so that when the free end is pulled in one direction through the lock, it cannot be pulled back in the other direction due to ratcheting means molded into the lock 134 and the free end 132. In this case, the free end may initially not pass through the lock, but the free end 132 is connected at a junction 133 to the cinching wire 108. (FIG. 8C.) The cinching wire is then threaded through the lock 134, and thence through the bore 107 of the push rod. At the junction 133 between the free end 132 and the cinching wire 108, a weakened frangible portion is provided so that a sharp tug on the cinching wire will break the junction at the frangible portion. In this regard, see FIG. 8A-FIG. 8C, where a frangible zone 133 is exemplified. In this embodiment, the frangible zone includes a length of the tie which has reduced thickness in relation to the thickness in the vicinity of the frangible zone. This reduced thickness gives rise to the result that, should the tie be tensioned to a threshold amount of force, then the tie will break at the frangible zone, and at no other place along the length of the tie.

Thus, as will be explained below, the operator is able to pull the arms of the capture element 110 closed until it adopts the configuration shown in FIG. 7 after the leaves 52, 54, 56 have been manipulated into position by moving the catheter 100. At this point, the operator gives the cinching wire a tug, which allows the cinching wire 108 to break away from the zip tie 130.

Figure 7:
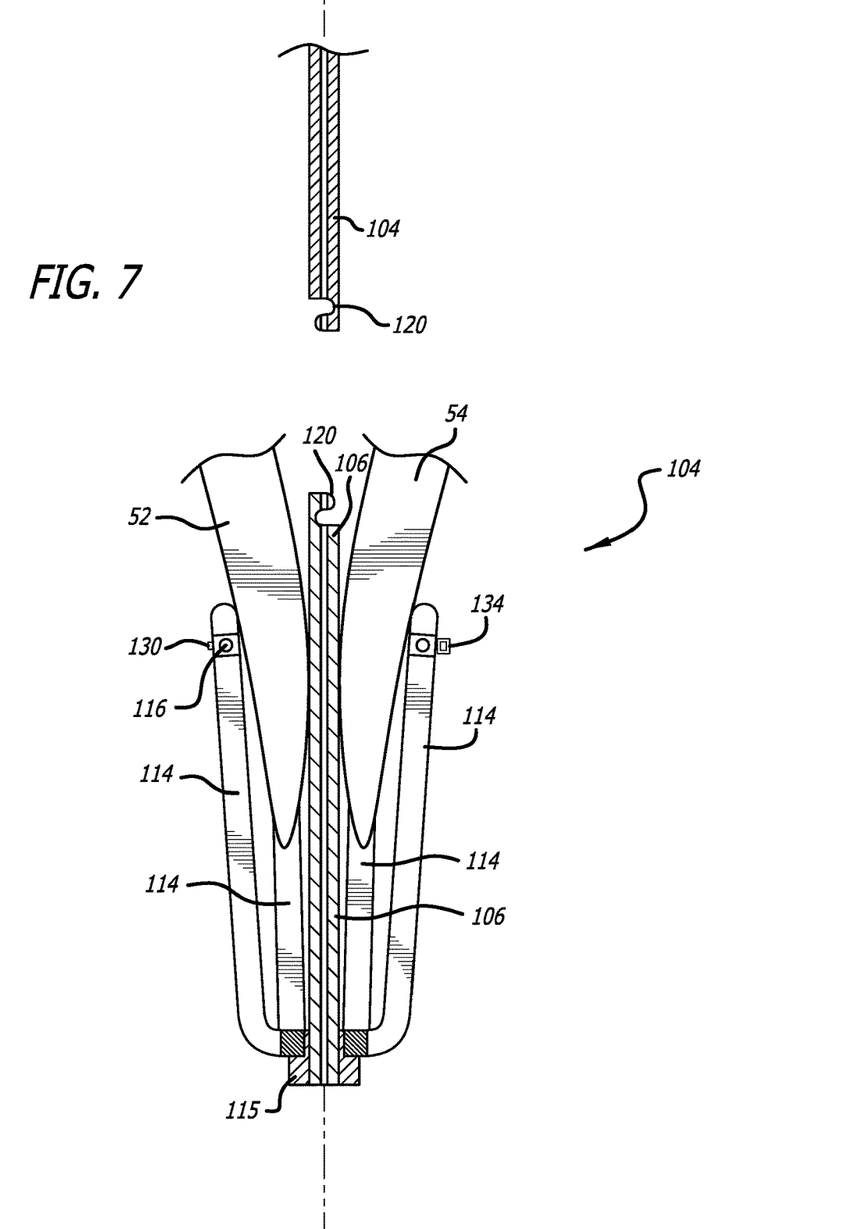
FIG. 7 is a sectional view of the system in FIG. 4, shown in a finally deployed condition.
Figure 8A:
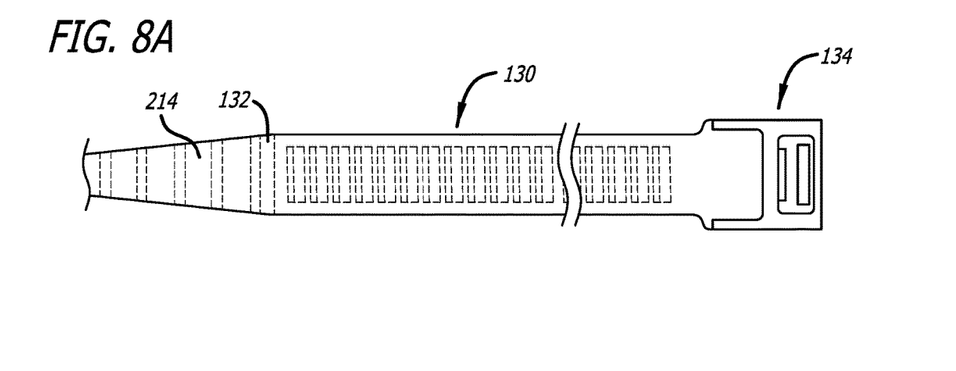
FIG. 8A is a view of a component of the invention seen in plan view.
Figure 8B:
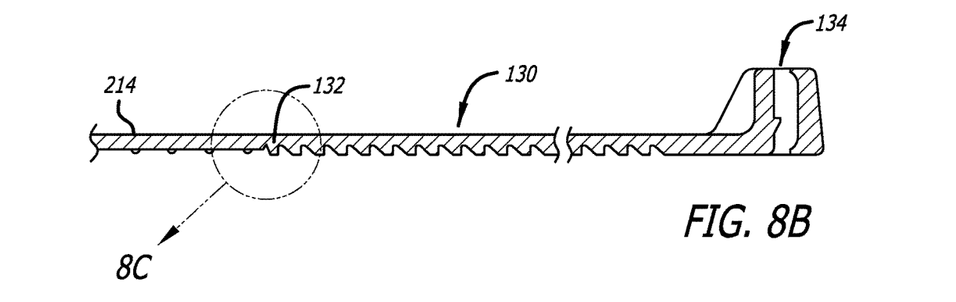
FIG. 8B is a view of the component in FIG. 8A, shown in side view.
Figure 8C:
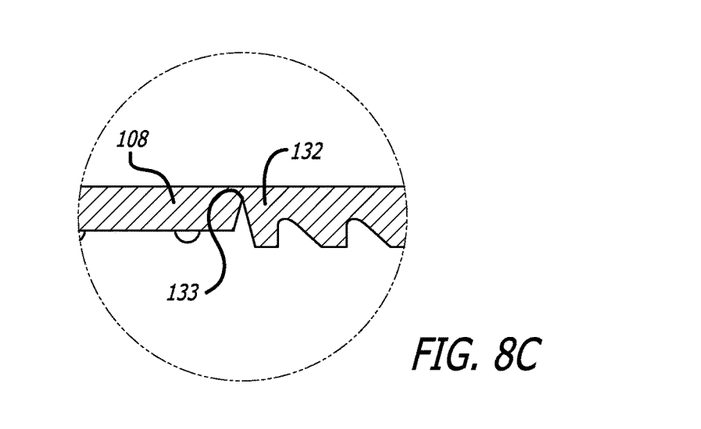
FIG. 8C is a detail view of a portion of the component circled in FIG. 8B, marked with the letters "8C."

An important feature of the push element 106 is that it includes a discontinuity 120, which may be understood with reference to FIGS. 4 and 7. The discontinuity is a discontinuity in the surface of the push element shaped in the form of clasping fingers so that, so long as the push element 106 remains in axial alignment, the discontinuity may transmit both a compression force and a tension force along the length of the push element. An inner sheath 122, slideable in relation to the push element 106, surrounds the push element 106 at the location of the discontinuity 120. It will be appreciated that, so long as the push elements remains contained within the inner sheath 122 the push element will maintain axial alignment. However, when the inner sheath 122 is withdrawn proximally to expose the discontinuity 120, then the push element 106 will tend to lose its axial alignment at the location of the discontinuity. At this point, the shape of the discontinuities allows a separation of adjacent portions of the push element at the location of the discontinuity to occur. This aspect has functional utility when the device 104 has been successfully deployed. Once this objective has been achieved, the operator withdraws the inner sheath 122 proximally from its position covering the discontinuity 120, to expose the discontinuity. The exposed push element 106 can no longer maintain axial alignment due to the absence of any constraining force, and so the discontinuity permits adjacent portions of the push element to separate from each other, leaving the device 104 behind in the patient, and allowing the remainder of the catheter to be withdrawn from the site of the procedure in the patient's heart. This will be explained in context of the method of using the invention, described below.

Deployment of the system 100 may take the following steps. The distal end of the catheter 100 is threaded into the right atrium of the heart of the patient according to known methodology until the system 100 contained in the distal end of the catheter is positioned directly above the tricuspid valve. (See for example, U.S. Pat. No. 8,475,525 which is incorporated herein by reference.) The distal end is then advanced gently through the three leaflets of the tricuspid valve into the right ventricle. See FIG. 3, where two leaflets 52, 54 are shown in relation to the system 100.

At this point, the sheath 102 is withdrawn proximally by a short distance, in relation to the push rod 106 and the device 104, sufficient to expose the device 104 and in particular the arms 114. It will be appreciated that once the arms are exposed, they will self-expand radially outwardly and will tend to assume the configuration that they were given during heat treatment. The shape they are given will be large enough to move slowly towards the tips of the leaflets 52, 54, 56 until each of the leaflets is contained within the basket-like structure of the capture element 110. At this point, the activation wire 108 is pulled taught by the user, by pulling on the free end located at the proximal end of the catheter using known control means. Pulling the activation wire 108 causes the tips of the arms 114 to reduce their circumferential distribution, and eventually causes the free end 132 of the zip tie to be passed into the lock 134.

At this point, the user is committed, because it is no longer possible allow the arms to expand by relaxing tension in the activation wire 108. The ratchet means inside the bridge 134 will prevent the zip tie 130 from moving backwards out of the bridge 134. Upon satisfying herself that the leaves are properly positioned, the user then proceeds to tension the zip tie 130 via the activation wire 108 until the tips of the leaves are forced up against the push element 106 and are confined in that position by the arms 114. In some embodiments, the push element in the region of the arms may be given a rough or barbed surface, to prevent the leaves from sliding out of their captured position. The same treatment may be given to the inside surfaces of the arms.

Then, when the leaves are fully captured by the arms 114 under tension of the zip tie 130, the user gives the activation wire 108 a sharp tug to break the connection 133 between the free end 132 of the zip tie and the activation wire 108. This allows the user to withdraw the activation wire out through the bore 107 of the push rod 106. Thereafter, the inner sheath 122 is pulled proximally in relation to the push rod 106 to expose the discontinuity 120. As explained above, the push rod can no longer maintain its axial alignment in the vicinity of the discontinuity, and the push rod separates into (a) a distal portion which acts as part of the capture mechanism described and (b) a proximal portion that can be withdrawn from the patient along with the catheter 100.

The device 104 is finally left within the patient in the configuration seen in FIG. 7, with the tips of the three leaves 52, 54, 56 captured at the point of their meeting in the center of the tricuspid valve 21, between the push element 106 on the inside, and by the arms 114 of the capture element 110 on the outside.

This action has the effect of tightening the leaflets along the lengths where they are contiguous with an adjacent leaf. The result is that the valve 21 now presents three separate bores for blood flow instead of only one. These three bores present a smaller cross sectional area for blood flow than a single bore. However, the improved coaptation of the leaflets is more efficient at preventing regurgitation, which is a highly desirable result.

Accordingly, there is described a novel system and method that addresses needs in the art for capturing and connecting the three contiguous points of a tricuspid heart valve. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A system for repairing a tricuspid valve in a patient's heart comprising:
   a post having a distal end and a proximal end;
   a capture element attached to the distal end of the post, the capture element including:
      a plurality of arms each having a first end and a second end, each arm attached at the first end to the post and extending both radially outwardly from the post and proximally, each arm defining an opening at the second end;
      a wire passing sequentially through the opening on each arm, whereby tensioning the wire draws the second end of each arm towards the post; and
   wherein the post defines a central bore having an orifice at the distal end of the post, and the wire passes into the bore through the orifice.

2. The system of claim 1, wherein the post at the proximal end is removably attached to a delivery catheter by an attachment means.

3. The system of claim 1, wherein the wire is attached to a zip tie by a frangible connection.

4. The system of claim 1, wherein the capture element is foldable about the post and both the post and the capture element are inserted inside an inner bore of a delivery catheter.

5. The system of claim 1, wherein the capture element further includes a hoop having a continuous circumference sized to receive the distal end of the post.

6. The system of claim 5, wherein the arms and the hoop of the capture element are formed from a single sheet of metal.

7. The system of claim 6, wherein the single sheet of metal is a Nickel Titanium alloy.

8. The system of claim 5, further including an annular plug inserted between the post and the hoop.

9. The system of claim 8, wherein the plug between the post and the hoop is formed by enlargement through applying a compression force across an axial dimension so as to expand a radial dimension of the plug.

10. A method of repairing a tricuspid valve having a first leaflet, a second leaflet, and a third leaflet in a heart of a patient, the method comprising:
    passing an elongate post between the first leaflet, the second leaflet, and the third leaflet;
    opening a wire into a circular shape that surrounds the post, thereby providing a space between the wire and the post;
    manipulating the post and the wire until a tip of the first leaflet, a tip of the second leaflet, and a tip of the third leaflet are positioned within the space between the wire and the post;
    applying a tension force to the wire, thereby reducing a circumference of the circular shape and thereby capturing simultaneously the tip of the first leaflet, the tip of the second leaflet, and the tip of the third leaflet between the post and the wire; and
    further including locking the wire into a fixed final circumference.

11. The method of claim 10, wherein locking the wire includes using a zip tie.

12. The method of claim 11, wherein using a zip tie includes breaking a frangible connector that attaches the wire to the zip tie.

13. The method of claim 10, wherein opening a wire into a circular shape includes releasing from confinement arms attached to the elongate post, wherein the arms carry the wire and are shaped to expand radially outwardly.

14. The method of claim 13, wherein releasing from confinement includes withdrawing a sheath away from covering the arms.

15. The method of claim 10, further including removing a delivery catheter from the heart of the patient, while leaving the post and the wire in the heart.

16. The method of claim 15, wherein removing a delivery catheter from the heart of the patient includes disconnecting the post from the delivery catheter by withdrawing a sheath away from covering a portion of the post.

* * * * *